(12) United States Patent
Sahari et al.

(10) Patent No.: US 7,688,429 B2
(45) Date of Patent: *Mar. 30, 2010

(54) DEVICE FOR THE ANALYSIS OR ABSORPTION MEASUREMENT OF A SMALL QUANTITY OF A LIQUID MEDIUM BY MEANS OF LIGHT

(75) Inventors: Thomas Sahari, Munich (DE); Holm Kandler, Auggen (DE)

(73) Assignees: Hellma GmbH & Co, KG, Mullheim (DE); Thomas Sahiri, Munich (DE)

( * ) Notice: Subject to any disclaimer, the term of this patent is extended or adjusted under 35 U.S.C. 154(b) by 448 days.

This patent is subject to a terminal disclaimer.

(21) Appl. No.: 10/599,744

(22) PCT Filed: Apr. 18, 2005

(86) PCT No.: PCT/EP2005/004083

§ 371 (c)(1),
(2), (4) Date: Oct. 6, 2006

(87) PCT Pub. No.: WO2005/114146

PCT Pub. Date: Dec. 1, 2005

(65) Prior Publication Data
US 2008/0106742 A1    May 8, 2008

(30) Foreign Application Priority Data
May 7, 2004    (DE) .................. 10 2004 023 178

(51) Int. Cl.
G01N 21/00    (2006.01)
(52) U.S. Cl. ........................ 356/72; 356/440

(58) Field of Classification Search .................. 356/72, 356/409, 432, 436, 440, 246
See application file for complete search history.

(56) References Cited

U.S. PATENT DOCUMENTS

| 3,141,094 | A | * | 7/1964 | Strickler | 250/574 |
| 3,164,663 | A | * | 1/1965 | Gale | 356/436 |
| 3,392,623 | A | | 7/1968 | Walker et al. | |
| 3,518,009 | A | | 6/1970 | Shamos et al. | |
| 3,734,622 | A | | 5/1973 | Adler | |

(Continued)

FOREIGN PATENT DOCUMENTS

EP    0660106    6/1995

(Continued)

*Primary Examiner*—Kara E Geisel
(74) *Attorney, Agent, or Firm*—Volpe and Koenig, P.C.

(57) ABSTRACT

A device (1) having integrated beam switching systems is provided which uses corresponding devices (7 and 9) and fiber optic light guides (10 and 11) for guiding the light (3) used for analysis of a liquid medium (2), for example in a spectrophotometer, a spectrofluorimeter or a similar measuring device, to a measuring point located on the device (1) and embodied as a receiving surface (4) for the medium, and back therefrom to the detector for the spectrophotometer, a spectrofluorimeter or the like. The receiving surface (4) forms a flat measuring point on the upper side of the device (1) and is closed by a cover-type detachable reflector (8) in the position of use. The reflector is in close contact with the sample of the medium (2) and can be removed before the application of the sample and for cleaning the measuring point.

14 Claims, 4 Drawing Sheets

U.S. PATENT DOCUMENTS

| | | | | |
|---|---|---|---|---|
| 4,188,126 A | * | 2/1980 | Boisde et al. | 356/440 |
| 4,643,580 A | | 2/1987 | Gross et al. | |
| 5,418,615 A | * | 5/1995 | Doyle | 356/436 |
| 5,438,420 A | * | 8/1995 | Harwick et al. | 356/440 |
| 5,557,103 A | * | 9/1996 | Hughes et al. | 250/255 |
| 5,569,923 A | * | 10/1996 | Weissman et al. | 250/341.2 |
| 5,678,751 A | * | 10/1997 | Buchanan et al. | 228/124.6 |
| 6,628,382 B2 | | 9/2003 | Robertson | |
| 6,817,754 B2 | * | 11/2004 | Tsang et al. | 374/20 |
| 7,170,608 B2 | * | 1/2007 | Burge | 356/440 |
| 2002/0110496 A1 | | 8/2002 | Samsoondar | |
| 2003/0081206 A1 | * | 5/2003 | Doyle | 356/301 |

FOREIGN PATENT DOCUMENTS

WO 03034026 4/2003

* cited by examiner

DEVICE FOR THE ANALYSIS OR ABSORPTION MEASUREMENT OF A SMALL QUANTITY OF A LIQUID MEDIUM BY MEANS OF LIGHT

BACKGROUND

The invention relates to a device for the analysis or absorption measurement of a small quantity of a liquid medium, for example, a drop, by means of light, which is guided through the medium and which then can be detected or analyzed photometrically, spectrophotometrically, fluorometrically, or spectrofluorometrically. The device has a receiving point area for depositing or applying drops of the medium at the top in the position of use, a horizontally oriented light inlet located underneath the receiving point in the position of use in its housing, and a first device located behind the light inlet in the beam path for guiding the light upwards towards the receiving point.

In many cases, only small quantities of liquid samples are available. This applies primarily in biochemical, medical, or pharmaceutical analysis. For systematic surveys with a plurality of similar samples, for example, titration plates as sample containers are used, which allow efficient, sequential, or parallel analysis.

For individual measurements for qualitatively very different substances and especially for absorption measurements, such samples are filled into cells and then analyzed, in a known way.

For cells with a measurement chamber volume of ten microliters and less—that is, approximately drop sized—due to the small substance quantity, it is difficult to introduce the sample of the liquid medium into the measurement channel, because suitable cells provide only small access openings and the measurement channel has a correspondingly small cross section. When introducing a sample of the medium to be analyzed into the measurement channel, it must be guaranteed that the channel is completely filled by the medium and, for example, that there are no bubbles within the volume of the liquid medium passed through by the measurement beam, because bubbles could considerably falsify the measurement results.

Therefore, cells are usually first filled outside of a corresponding measurement device and the quality of the filling is checked visually. Then the cell is inserted into the cell holder of a measurement device. Here, the cell must be positioned in the measurement beam, so that there is no variation in the absorption level in the cell itself due to the screening effect of the measurement chamber cross section, because such variation could also falsify the measurement results. This can occur because the beam cross section of a spectrophotometer used as the measurement device usually exceeds the free aperture of the mentioned cell with very small sample volumes. Even small deviations in the positioning of the cell in comparison with a reference measurement or through the use of several cells, which are structurally identical but subject to variation in manufacturing, within one measurement cycle can lead to deviation in the measurement values. After the measurement, due to the shape of the cell holder in commercially available measurement devices it is practically unavoidable to be required to remove the cells from the holder for emptying and cleaning.

From DE 33 44 387 A1 a photometer head for small measurement volumes is known, in which a pair of light transmitters and light receivers is arranged in a material block and this material block has a recess, which is covered with a plate, in the area of facing surfaces of the light transmitter and light receiver. This plate has a bore, through which an application device can be guided with a spacing between the facing surfaces of the light transmitter and light receiver. Therefore, the use of a cell is to be avoided. The drop of the liquid medium to be analyzed is to be introduced into this spacing and must be held there despite the force of gravity acting on it. Thus, the application of a sample drop must be carried out with great care, so that this drop is held stationary in the spacing, which is open at the bottom, between the surfaces despite the force of gravity, which incidentally also requires a corresponding consistency of the medium to be analyzed.

SUMMARY

Therefore, there is the objective of creating a device of the above-noted type, in which a small sample quantity of a liquid medium can be placed in a simple way at a measurement point and which allows reliable and simple cleaning after the measurement. Furthermore, a reference measurement should be possible, without the measurement conditions being able to change between the reference measurement and the sample measurement, which would be disadvantageous for the measurement result.

To meet this objective, the device defined above is characterized in that the device has a reflector that can be attached detachably above the receiving point; in that, in its position of use, the reflector has a defined spacing from the receiving point, which is filled or can be filled with the medium at least in the area of the light passage; and in that a second device is provided for guiding the light coming from the reflector towards a detector.

Thus, for this device the medium to be analyzed can also be deposited or applied in drops in very small quantities onto an essentially horizontal surface, with the light passing through this receiving point at least once. This can be the case on the way towards the reflector or from the reflector, wherein, however, advantageously a correspondingly large measurement distance is given when the light is guided through the sample both on its way to the reflector and also coming from this reflector.

Because the medium can be deposited on a top receiving point area, it requires no special care and no special precautions to avoid the negative effects of the force of gravity. Instead, the force of gravity even helps to hold the medium in its position, in which the measurement is to be performed. In this way, complicated filling in a measurement channel can also be avoided. All that is necessary is to remove the detachable reflector, to deposit the sample onto the receiving or measurement point, and to bring the reflector into its position of use, in order to be able to then perform the measurement. Thus, the device is also suitable for effective execution of individual measurements on small and very small quantities of the medium to be analyzed. Furthermore, matching measurement conditions are given for all of these measurements, so that there are no disadvantageous changes between the reference measurement and the sample measurement. Here, applying drops of a sample, for example, by means of a pipette, is an extremely simple process to perform.

Preferably, the receiving point can be accessed from above as a surface and the medium to be analyzed can be fixed or held at the receiving point by the force of gravity.

Here, it is preferable when the receiving point has large enough dimensions that the light passing through this point towards the reflector and reflected back from this reflector is guided at least once, in particular twice, through the receiving point and/or through the medium. In the latter case, a measurement distance is produced that corresponds to twice the distance of the receiving point from the reflector, which allows effective measurements and analyses.

A configuration of advantageous significance can be provided in that a light guide or a light-guiding fiber bundle is arranged for guiding the light from the first device towards the receiving point and, in particular, a light guide or a fiber bundle guiding the light is arranged between the receiving point and the second device for guiding the light coming from the reflector and the sample. In this way, the receiving point struck by the light or the effective measurement spot on the receiving point can be kept small, which simultaneously means the best possible use of the light. This applies even when the light makes two passes through the sample to be measured, namely on its way towards the reflector and on its way back from the reflector. With the help of the mentioned light guide or light-guiding fiber bundle, the light beams can be concentrated on a very small space.

Here, the targeted guidance of the light can be improved, in that, underneath the receiving point for the medium, there are optics, at least one convergent lens, which bundle the light and which is optically coupled with the light guide(s). Such optics can be combined both with the light guide coming from the first device for guiding the light and also with the light guide leading to the second device for guiding the light. However, it is also possible to provide common optics for the two light guides or fiber bundles located close together at their ends.

An especially advantageous configuration of the invention for limiting the lateral expansion of the receiving point and thus for further reducing the necessary quantity of medium to be analyzed can be provided in that the receiving point is an area recess on the top side of the device underneath the reflector and, in particular, is formed by the boundary of the optics or lens facing the receiving point or by the light guide ending at this boundary, with the lens or the optics and/or the ends of the light guides being set back relative to the top side of the holder for the lens or the optics or the light guides. In a preferred embodiment, the receiving point can be limited at the sides so that it is a recess or is arranged in a recess, which can preferably be formed so that the optics or lens or the ends of the light guides are arranged somewhat recessed or set back relative to the topmost boundary or surface of its holder, so that, in this way, the corresponding recess is formed automatically.

Here, it is preferred when the lens or optics coupled—at least optically—to the light guides are formed simultaneously as the closing window of the device, on which the sample of the medium to be analyzed can be dropped. Thus, these features and possibilities produce a device, which can be operated very easily and on which a very small quantity of a medium can be deposited by drops, which produces a very simple operation. Nevertheless, this sample can also be passed through very effectively by light, which can be measured or detected easily.

The reflector can be a mirror or a reflecting prism and can contact the sample without a gap in the position of use. The sample is passed through by the light in a correspondingly effective way and is guided back from the reflector, in order to reach the actual detector via the second guiding device. The measurement distance through the sample can be twice as large as the distance of the receiving surface from the surface of the reflector and the light can cover twice this distance, as already mentioned above.

For a constant accuracy of the measurements and for avoiding changes in the measurement conditions between the individual measurements and also relative to the reference measurements, it is especially preferred when the reflector, which can be set or attached detachably, is locked in rotation and centered relative to the device and its housing in the position of use. In this way, it is guaranteed that it is always attached in the same position relative to the device and its housing and thus also to the receiving point after a sample has been deposited. The relevant reflection conditions match accordingly. Here, different structural possibilities are given for guaranteeing the torsional strength, even though the reflector can be removed from its position of use.

So that the reflector achieves the prescribed distance to the receiving point in a repeatable way in the position of use, this distance can be set by at least one spacer between the reflector and housing or by a stop. Thus, the user does not need to take any precautions for maintaining the prescribed distance when placing the reflector on the device in the position of use. The formation of the spacer or a stop can also be solved structurally in different ways. Here, under some circumstances it is even conceivable that the spacer and the holder for the torsional strength of the reflector are combined together.

The irradiation of light to the device can be realized in any way and also the detection can interact in a suitable way with the light outlet from the device, wherein any measurement devices can be used.

However, it is especially preferred when the device has the external dimensions of a cell, which can fit into a photometer, spectrophotometer, fluorometer, or spectrofluorometer, and which can be struck by light, and when the devices arranged in the interior of the device are arranged for guiding or directing light to the point of the device, at which inlet and outlet windows for the light used for the measurement are provided in conventional cells, wherein the first device for guiding light directs the light emitted by the photometer towards the receiving surface and the second device for guiding light directs the light coming back from the measurement point towards the detector. Through skillful selection of the dimensions of the device according to the invention, this device can be inserted into common photometers, spectrophotometers, fluorometers, or spectrofluorometers, in order to be able to be used for measuring also very small samples of a medium in terms of quantity. This considerably reduces primarily the investment and installation costs.

It is favorable when the device is made from glass or plastic and has in the area of the light inlet, as a first guiding device, a tilted prism or a tilted mirror facing a shaft or channel at a right angle to the light inlet for a light guide or a light-guiding fiber bundle and in parallel another light guide with a second tilted prism or tilted mirror placed at its opening, which lies opposite an outlet window for the light or which forms this window.

In this way, the light inlet and light outlet correspond to a commercially available cell, so that the supply line of the light and also its detection after passing through the sample can be performed very easily primarily in corresponding, already existing measurement devices.

For example, the outer dimensions of the cross section of the device can correspond to those of a standard cell and can equal, in particular, 12.5 millimeters by 12.5 millimeters.

It should still be mentioned that the light beam emerging again from the device is aligned with the inlet light beam or can enclose a right angle with this beam. The latter is primarily preferably for fluorometers or spectrofluorometers.

Primarily through the combination of individual or several of the previously described features and measures, a device is produced, which is defined above and which allows simple handling and analysis also for very small quantities of a liquid medium, independent of its viscosity. Even media of relatively high viscosity can be easily analyzed, because these media can be held without a problem on the essentially horizontal receiving surface. Furthermore, after a measurement is performed, cleaning is carried out very easily and can be carried out, for example, with the help of optics cleaning cloths or pads. If necessary, typical cleaning agents can be used here. It is favorable that the measurement point acted upon by the medium to be analyzed can be accessed very easily, wherein the device can even remain in the measurement device.

As a whole, a device is produced, which can be used primarily in a configuration with cell-like dimensions in most commercially available measurement devices and here also in older measurement devices without modification. Reference measurement, sample measurement, and cleaning can be carried out with no interruptions with low expense and without significant time losses.

BRIEF DESCRIPTION OF THE DRAWINGS

Below, embodiments of the invention are described in more detail with reference to the drawing. Shown in partially schematized representation.

DETAILED DESCRIPTION OF THE PREFERRED EMBODIMENTS

In the following description, parts that are equivalent in terms of their function but that are in different embodiments have been indicated matching reference numbers, even if their shape has been somewhat modified.

A device designated as a whole with 1, whose housing 6 and thus also whose housing contents are shown in a longitudinal section in FIGS. 1, 2, 5, and 6, is used for the analysis or absorption measurement of a small quantity, for example, a drop, of a liquid medium 2 using light, symbolized by arrows 3. This light is guided through the medium 2 and then detected or analyzed in a known way photometrically, spectrophotometrically, fluorometrically, or spectrofluorometrically.

Primarily in the common view of FIGS. 1 to 4, it can be seen that the device 1 has an essentially horizontal and flat receiving point 4 area at the top in the position of use for depositing or applying drops of the medium 2, a light inlet 5 oriented horizontally in the position of use and located underneath the receiving point 4 in its housing 6, and a first device 7 located in the beam path behind the light inlet 5 for guiding the light upwards towards the receiving point 4, and also a reflector 8 that can be detachably attached above the receiving point 4. Here, in the position of use, this reflector 8 has a defined spacing from the receiving point 4, in order to produce a constant precise measurement distance for the light. According to FIG. 4, this spacing is filled or can be filled by the medium 2 at least in the area of the light passage. Furthermore, the device 1 has a second device 9 for guiding the light coming from the reflector 8 towards a detector, which is not shown in more detail in FIGS. 1 and 2.

Figure 1:
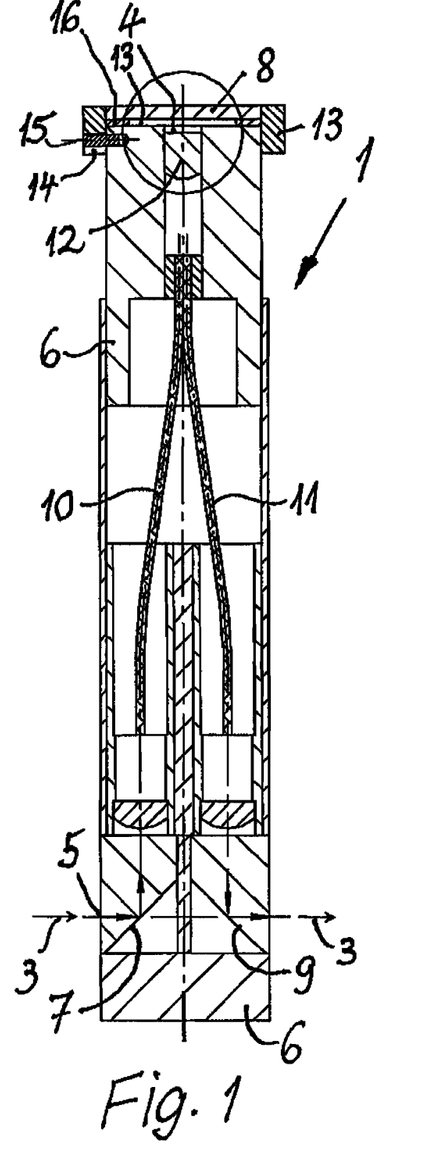
FIG. 1 a longitudinal section of a device according to the invention with its housing, in which a light beam is input horizontally and directed upwards in the vertical direction by a first device, wherein a top receiving point area is provided for depositing the medium to be analyzed, above which a detachably fastened reflector is located, from which the light is led via a second light guide to a second device for guiding light back out of the device, wherein the receiving point is formed by optics bundling the light, FIG. 2 a representation corresponding to FIG. 1 for a modified embodiment, at which the light guide leads up to the receiving point area for the medium to be analyzed, FIG. 3 at an enlarged scale, the detail indicated in FIG. 1 by a circle for a reflector that is still removed, after a sample has been deposited, FIG. 4 a representation corresponding to FIG. 3 after the reflector has been mounted in its position of use, in which it contacts the sample without a spacing and is located with its surface facing the sample at a defined distance to the receiving point, through which the light passes, FIG. 5 the arrangement of a device according to the invention from FIG. 1 in a receiving shaft of a photometer or a similar measurement device defined for cells, and FIG. 6 a representation corresponding to FIG. 5 with a device according to FIG. 2.
Figure 2:
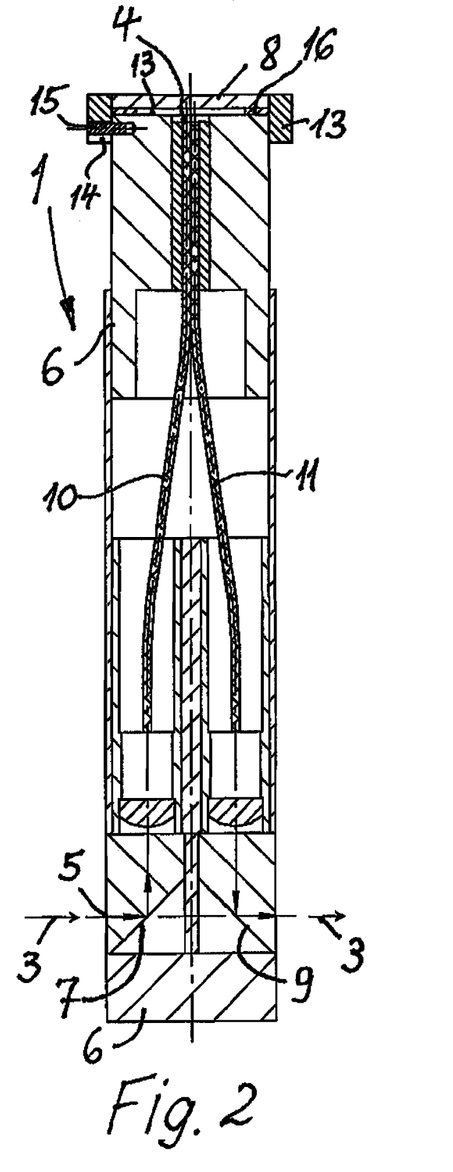
Figure 3:
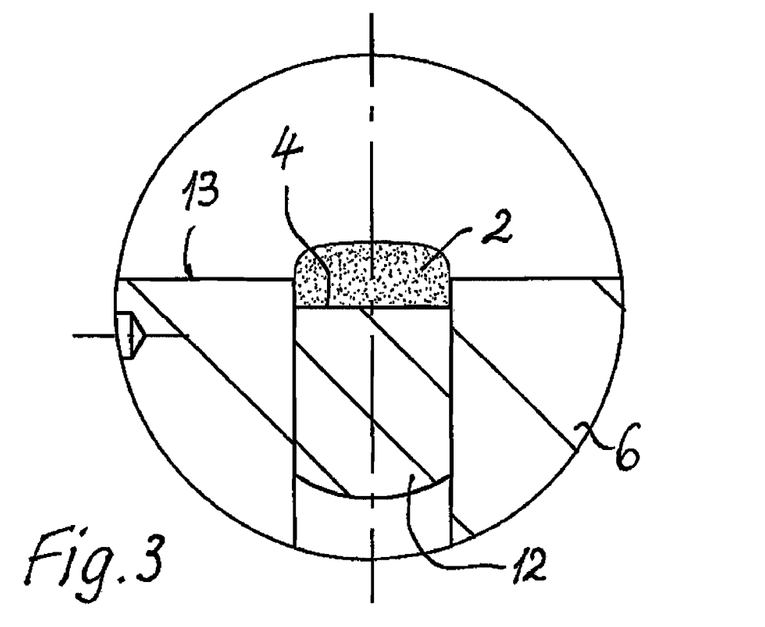

With reference to FIGS. 1 to 3 and here primarily FIG. 3, it becomes clear that the receiving point 4 can be accessed from above as a surface and the medium 2 to be analyzed can be fixed and held at this receiving point 4 by the force of gravity. Here, this receiving point 4 has dimensions so large that the light 3 moving towards the reflector 8 and reflected back from this reflector is guided at least once, and in both embodiments twice, through the receiving point 4 and through the medium 2. In this way, it is achieved that the measurement distance through the sample formed by the medium 2 is twice as large as the spacing of the receiving surface 4 from the surface of the reflector 8 and the light covers this spacing twice. In this way, the measurement distance can be twice as large as the mentioned spacing.

Figure 5:
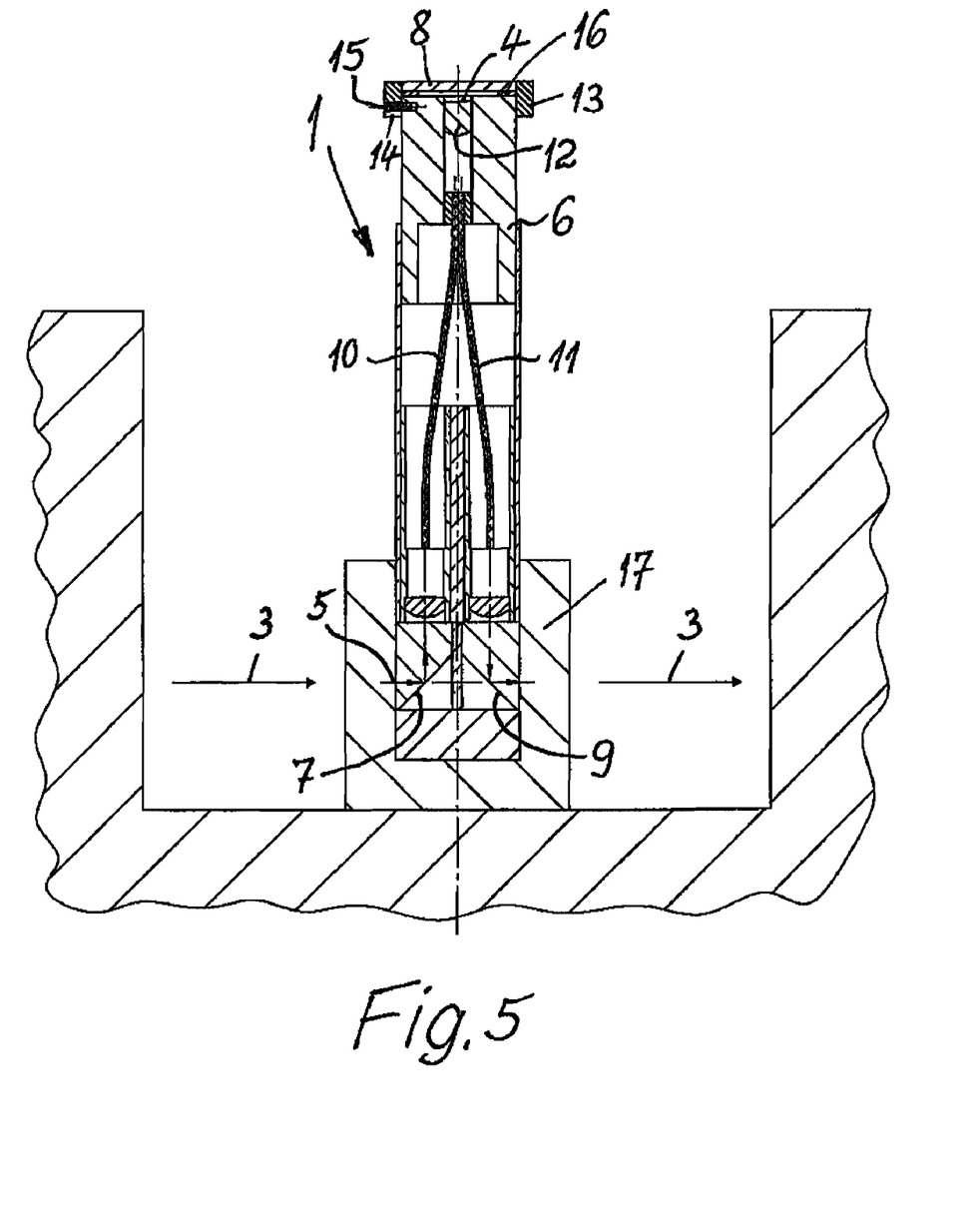
Figure 6:
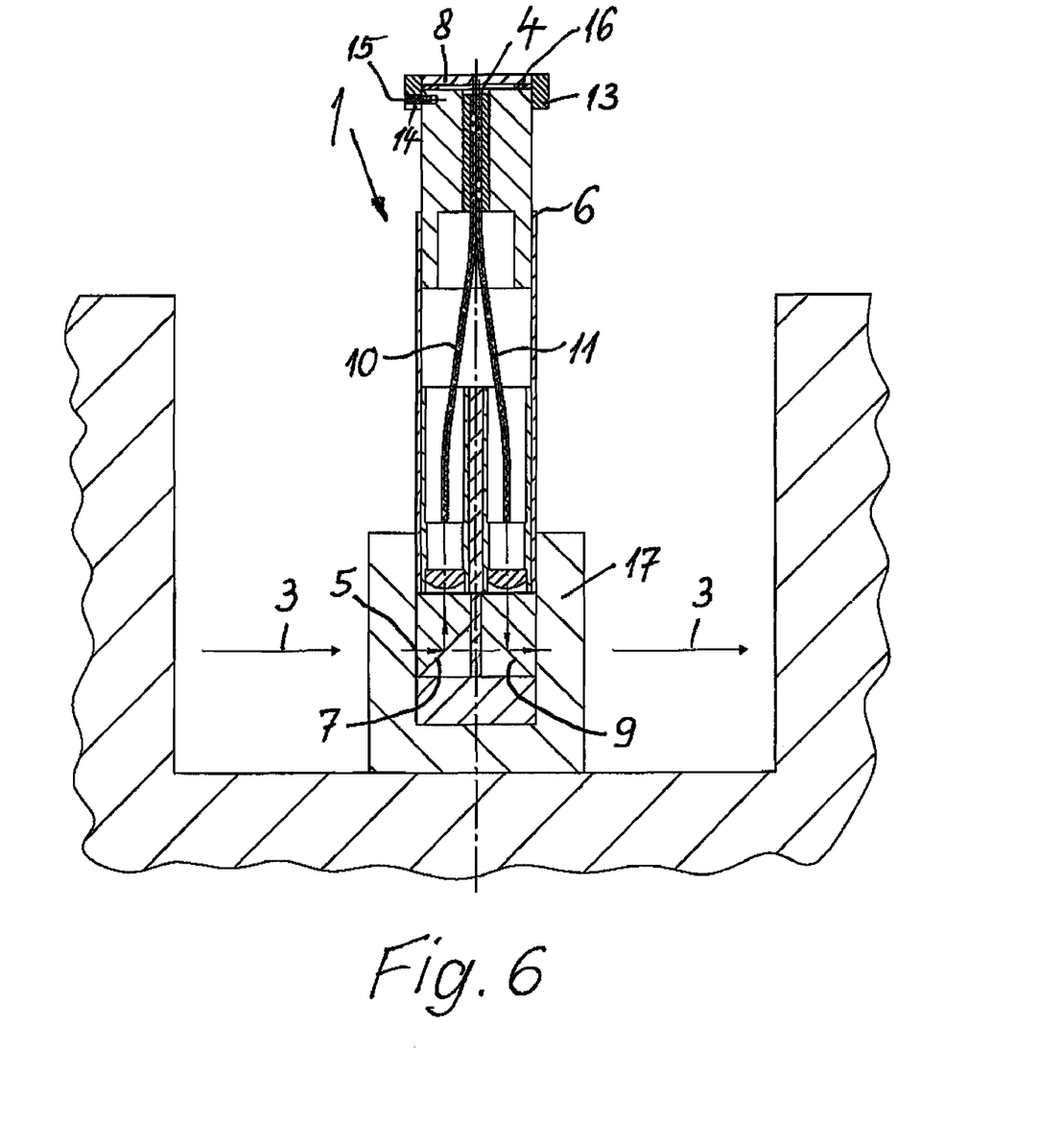

In both embodiments according to FIGS. 1 and 5, on one hand, and also according to FIGS. 2 and 6, on the other hand, a light guide or light guiding fiber bundle 10 is arranged for guiding the light from the first device 7 towards the receiving point 4, and similarly a light guide or a fiber bundle 11 guiding the light is arranged between the receiving point 4 and the second device 9 for guiding the light coming from the reflector 8 and from the sample, so that the light can reach the receiving point 4 and the medium 2 provided as a sample effectively and with the lowest possible losses.

According to FIGS. 1, 3, 4, and 5, underneath the surface area receiving point 4 for the medium 2 there are optics 12, for example, a convergent lens, which bundles the light and which is optically coupled with the light guides 10 and 11.

In contrast, in the embodiment according to FIGS. 2 and 6, the light guides 10 and 11 extend directly up to the receiving point 4.

In both embodiments, the receiving point 4 is an area recess on the top side of the device 1 underneath the reflector 8. In the embodiment according to FIGS. 1, 3, and 4, this receiving point 4 is formed by the boundary of the optics or lens 12 facing it, and in the embodiment according to FIG. 2 by the light guides 10 and 11 ending at this position, wherein the lens or optics 12 and/or the ends of the light guides 10, 11 are set back relative to the top side 13 of the holder for the lens or the optics or the light guides or relative to the top side 13 of the housing 6. The setting back of the optics 12 for forming the somewhat recessed receiving point 4 can be seen particularly well primarily in FIGS. 3 and 4. Thus, the sample of the liquid medium 2 is also bounded and held towards the sides, to which its surface tension can also contribute. Thus, on a very small space a defined small quantity of a few microliters can be fixed and analyzed and detected by means of light.

Figure 4:
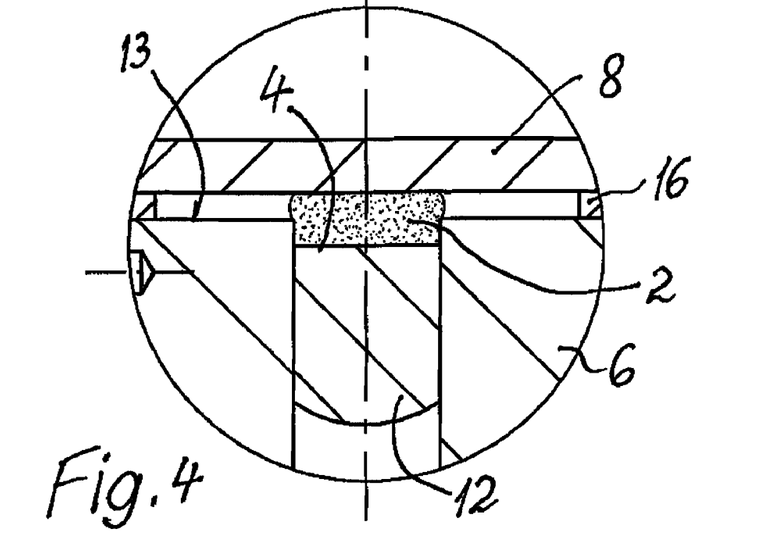

In this embodiment according to FIGS. 3 and 4, the lens or optics 12 coupled with the light guides 10 and 11 are simultaneously formed as the closing window of the device 1, on which the sample of the medium 2 to be analyzed can be applied in drops. Accordingly, the operation and accessibility both for applying the sample and also for later cleaning is easy and simple.

In the embodiment, the reflector 8 is a mirror, but could also be a reflecting prism, and according to FIG. 4 touches the sample without spacing in the position of use.

Here, the reflector 8, which can be set or detachably attached, is locked in rotation and centered relative to the device 1 and its housing 6 in the position of use. This is realized, for example, in FIGS. 1 and 2 by an edge 13 on the reflector 8 overlapping the housing 6, which has at least one open edge slot 14 that is open downwards, with which a projection or pin 15 connected to the housing 6 or the device 1 can be overlapped. While the edge 13 provides the centering function, with the help of the slot 14 and the projection or pin 15 the torsional strength can be implemented. Here, the pin—eccentric to the optics 12—could also run through the entire device 6 and could interact at an opposite end with a second slot 14 of the edge 13 of the reflector 8 opening downwards.

The spacing of the reflector 8 from the receiving point 4 is set in the embodiment by an annular spacer 16, which is arranged and, in particular, fixed between the reflector 8 and top side 13 of the housing 6. However, there could also be some other stop for the reflector 8, which also interacts, if necessary, indirectly with its edge 13. Instead of a peripheral spacer 16 arranged like a ring on the reflector in the area of the edge 13, there could also be individual spacer pieces. Here, it is especially favorable when this spacer 16 is connected to the reflector 8, so that after removing the reflector, the top side 13 and the receiving point 4 are accessible unimpaired for cleaning.

In FIGS. 5 and 6, an especially preferred configuration of the devices 1 is shown, wherein both the device according to FIG. 1 and also that according to FIG. 2 have outer dimensions of a cell that can be struck by light and that can be used in a photometer, spectrophotometer, fluorometer, or spectrofluorometer. In each of FIGS. 5 and 6, one can see a receiving shaft 17 of such a photometer, spectrophotometer, fluorometer, or spectrofluorometer, which are each shown only greatly schematized. Here, the devices 7 and 9 arranged in the interior of the device 1 for feeding or guiding light to the point of the device 1, at which inlet and outlet windows are provided in typical cells for the light 3 used for the measurement, wherein the first device 7 for guiding light directs the light emitted from the photometer or the like towards the receiving surface 4 and the second device 9 for guiding light directs the light from the measurement point and returning to the reflector towards the detector.

Thus, for corresponding dimensions of the device 1, this device can be used in existing measurement devices, which increases its applicability, because they are suitable for also analyzing small and very small quantities of a medium 2. Here, it is preferable when the outer dimensions of the cross section of the device 1 correspond to a standard cell and equal, in particular, 12.5 mm×12.5 mm, because the majority of photometers or similar measurement devices are formed for such dimensions. Here, the outgoing light beam can be aligned with the incoming light beam, as is shown in FIGS. 1 and 2 and also in FIGS. 5 and 6. However, it is also possible that the outgoing light beam encloses a right angle with the incoming light beam in an approximately horizontal plane, which is useful primarily in fluorometers.

It should also be mentioned that the device 1 is preferably composed of glass or plastic and has, in the area of the light inlet 5, as a first guiding device 7, a tilted prism or a tilted mirror facing a shaft 18 or channel at a right angle to the light inlet for the light guide 10 and parallel to this light guide another light guide 11 with a second tilted prism or tilted mirror, which is arranged at the opening of the other light guide and which is opposite an outlet window for the light or forms this window. Here, the second light guide 11 also extends into a shaft or channel 18.

The device 1 has integrated beam steering with the help of corresponding devices 7 and 9, as well as fiber-optic light guides 10 and 11 for guiding the light 3 used for the analysis of a liquid medium 2, for example, in a spectrophotometer, spectrofluorometer, or a similar measurement device towards the measurement point located on the device 1 and formed as a receiving surface 4 for the medium and from this point back towards the detector of the spectrophotometer, spectrofluorometer, or the like. Here, this receiving point 4 is provided as a measurement point area on the top side of the device 1 and closed in the position of use by a cover-like, detachable reflector 8, which also touches the sample or the medium 2 without spacing and can be removed before applying the sample and also for cleaning the measurement point.

The invention claimed is:

1. Device (1) for the analysis or absorption measurement of a small quantity of a liquid medium (2) using light (3), which is guided through the medium (2) and then can be detected or analyzed photometrically, spectrophotometrically, fluorometrically, or spectrofluorometrically, wherein the device (1) comprises a receiving point (4) area at a top thereof for depositing or applying the medium (2) in drops, a light inlet (5) oriented horizontally and located underneath the receiving point (4) in a housing (6), and a first device (7) located downstream of the light inlet (5) and defining a beam path for guiding the light received by the light inlet (5) upwards towards the receiving point (4), the device (1) has a reflector (8), which is attached detachably above the receiving point (4) opposite from the beam path extending from the light inlet; the reflector (8) has a defined spacing from the receiving point (4), which is filled or can be filled by the medium (2) at least in an area aligned with the beam path of the first device (7); and a second device (9) is provided for guiding the light coming from the reflector (8) towards a detector, a light guide or light-guiding fiber bundle (10) is arranged for guiding the light towards the receiving point (4) from the first device (7) and a light guide or a fiber bundle (11) for guiding the light coming from the reflector (8) and the sample is arranged between the receiving point (4) and the second device (9), optics (12) comprising at least one convergent lens, which bundles the light and which is coupled optically with at least one of the light guide for guiding the light towards the receiving point (4) or the light guide for guiding the light coming from the reflector (8), is provided underneath the receiving point (4) for the medium (2), and the receiving point (4) is an area recess on the toy side of the device (1) underneath the reflector (8) and is formed by a boundary of the optics (12) facing the receiving point, wherein the boundary of the optics (12) is recessed relative to a toy side (13) of a holder for the optics (12).

2. Device according to claim 1, wherein the receiving point (4) has an externally accessible upper surface area and the medium (2) to be analyzed can be fixed or held by a force of gravity at the receiving point (4).

3. Device according to claim 1, wherein the receiving point (4) has dimensions such that the light (3) moving through the receiving point towards the reflector (8) and reflected back from the reflector is guided at least once through the receiving point (4) and/or through the medium (2).

4. Device according to claim 1, wherein the optics (12) coupled with the light guides (10, 11) are simultaneously formed as a closing window of the device (1), on which the sample of the medium (2) to be analyzed can be applied in drops.

5. Device according to claim 1, wherein the reflector (8) is a mirror or a reflecting prism and touches the sample of the medium (2) without spacing in the position of use.

6. Device according to claim 1, wherein the measurement distance through the sample is twice as large as a spacing of the receiving surface (4) from a surface of the reflector (8) and the light travels twice through the spacing.

7. Device according to claim 1, wherein the reflector (8) is rotatably fixed with and centered relative to the device (1) and the housing (6).

8. Device according to claim 6, wherein the spacing of the reflector (8) from the receiving point (4) is set by at least one spacer (16) between the reflector (8) and the housing (6) or a stop.

9. Device according to claim 1, wherein the device (1) has outer dimensions corresponding to outer dimensions of a standard cell, adapted for use in a photometer, spectrophotometer, fluorometer, or spectrofluorometer and receives light therefrom, and the first and second devices (7, 9) are positioned in the device (1) such that the first device (7) for guiding light directs the light emitted by the photometer, spectrophotometer, fluorometer, or spectrofluorometer towards the receiving surface (4) and the second device (9) for guiding light directs the light coming back from the measurement point towards the detector.

10. Device according to claim 1, wherein the device is comprised of glass or plastic, the first guiding device (7) comprises a tilted prism or a tilted mirror facing a shaft (18) or channel at a right angle to the light inlet for a light guide (10) and the second guiding device (9) comprises a second tilted prism or a tilted mirror facing a shaft or a channel at a right angle to a light outlet of the light guide or a fiber bundle (11) for guiding the light coming from the reflector (8).

11. Device according to claim 1, wherein the outer dimensions of a cross section of the device (1) correspond to dimensions of a standard cell.

12. Device according to claim 1, wherein the outgoing light beam is aligned with the incoming light beam or encloses a right angle with the incoming beam.

13. Device according to claim 11, wherein the outer dimensions equal 12.5 mm×12.5 mm.

14. Device (1) for the analysis or absorption measurement of a small quantity of a liquid medium (2) using light (3), which is guided through the medium (2) and then can be detected or analyzed photometrically, spectrophotometrically, fluorometrically, or spectrofluorometrically, wherein the device (1) comprises a receiving point (4) area at a toy thereof for depositing or applying the medium (2) in drops, a light inlet (5) oriented horizontally and located underneath the receiving point (4) in a housing (6), and a first device (7) located downstream of the light inlet (5) and defining a beam path for guiding the light received by the light inlet (5) upwards towards the receiving point (4), the device (1) has a reflector (8), which is attached detachably above the receiving point (4) opposite from the beam path extending from the light inlet; the reflector (8) has a defined spacing from the receiving point (4), which is filled or can be filled by the medium (2) at least in an area aligned with the beam path of the first device (7); and a second device (9) is provided for guiding the light coming from the reflector (8) towards a detector a light guide or light-guiding fiber bundle (10) is arranged for guiding the light towards the receiving point (4) from the first device (7) and a light guide or a fiber bundle (11) for guiding the light coming from the reflector (8) and the sample is arranged between the receiving point (4) and the second device (9), and the receiving point (4) is an area recess on the top side of the device (1) underneath the reflector (8) and is formed by the light guides (10, 11) ending at the receiving point position, wherein the ends of the light guides (10, 11) are recessed relative to a top side (13) of a holder for the light guides.

* * * * *

UNITED STATES PATENT AND TRADEMARK OFFICE
CERTIFICATE OF CORRECTION

PATENT NO. : 7,688,429 B2  Page 1 of 1
APPLICATION NO. : 10/599744
DATED : March 30, 2010
INVENTOR(S) : Thomas Sahiri and Holm Kandler It is certified that error appears in the above-identified patent and that said Letters Patent is hereby corrected as shown below:

| | | |
|---|---|---|
| On the Title | Item 12 | Sahari et al. must be Sahiri et al. |
| | Item 75 | Thomas Sahari must be Thomas Sahiri |
| Column 8 | Line 52 | on the toy must be on the top |
| | Line 55 | to a toy must be to a top |
| Column 10 | Line 12 | at a toy must be at a top |

Signed and Sealed this

Twenty-second Day of June, 2010

David J. Kappos
*Director of the United States Patent and Trademark Office*